United States Patent [19]
Feldman et al.

[11] 4,096,149
[45] Jun. 20, 1978

[54] HYDROLYSIS OF NITRILES

[75] Inventors: Julian Feldman; David W. Smith, both of Cincinnati, Ohio

[73] Assignee: National Distillers and Chemical Corporation, New York, N.Y.

[21] Appl. No.: 521,014

[22] Filed: Nov. 5, 1974

[51] Int. Cl.² ............... C07D 213/57; C07C 103/127; C07C 103/133; C07C 103/22
[52] U.S. Cl. ............................ 260/295.5 A; 260/404; 260/558 R; 260/561 R; 260/561 HL; 260/561 N; 260/561 B
[58] Field of Search ..................... 260/295.5, 558, 557, 260/559, 561, 429, 295.5 A, 558 R, 561 R, 561 N, 561 HL, 561 B, 561 K, 404; 252/435, 437

[56] References Cited

U.S. PATENT DOCUMENTS

| | | | |
|---|---|---|---|
| 3,673,250 | 6/1972 | Rauch et al. | 260/561 N |
| 3,801,639 | 4/1974 | Fanelli et al. | 260/561 N |
| 3,821,300 | 6/1974 | Rauch et al. | 260/561 R |
| 3,884,975 | 5/1975 | Fanelli et al. | 260/561 R |

*Primary Examiner*—Alan L. Rotman
*Attorney, Agent, or Firm*—Kenneth D. Tremain

[57] ABSTRACT

Nitriles, such as acrylonitrile, are converted to the corresponding amides by a catalytic hydrolysis employing as the heterogeneous catalyst, the reaction product of a rhodium compound and a thiophosphite supported on a solid support.

13 Claims, No Drawings

HYDROLYSIS OF NITRILES

BACKGROUND OF THE INVENTION

It is well known that amides of organic carboxylic acids of the general formula RCONH$_2$ can be prepared from the corresponding acids, esters or acid chlorides by suitable reaction with ammonia. In many instances, the preferred method is to convert the nitrile to the amide by hydrolysis which proceeds in the presence of either acid or base. In most instances, however, it is difficult to isolate the amide because the hydrolysis continues further to form the corresponding acid. This is a result of the fact that the rate of hydrolysis of the amide is faster than that of the nitrile. An alternative procedure is to employ a strong acid, such as cold concentrated sulfuric acid, with the nitrile. This procedure has the disadvantage of requiring a molar excess of acid, and base equivalent to the acid, in order to liberate the amide. Another proposal has been to use an alkaline peroxide but at least an equivalent of peroxide is needed and its high cost makes this method unattractive for commercial usage.

More recently, catalytic processes have been developed for the preparation of amides from nitriles. For example, Goetz et al. U.S. Pat. No. 3,670,021 teaches the conversion of organic nitriles to amides by carrying out the hydrolysis reaction in the presence of a noble metal compound such as rhodium chloride which may be employed in the form of a complex thereof with, for example, pyridine, triphenylphosphine, 2,2'-bipyridyl, o-phenanthroline, and the like. A similar process is disclosed in Rauch et al. U.S. Pat. No. 3,673,250 in which a transition metal compound such as rhodium chloride is complexed with an organic phosphine, phosphite such as trialkyl or triarylphosphite, arsine, arsenite, stibine, or antimonite. While these catalysts, and particularly the Rauch et al. catalysts, exhibit a high initial productivity, a rapid deactivation of the catalyst has been observed.

We have now found a new catalyst system which is useful for the conversion of nitriles into amides with excellent conversions and selectivities and which exhibits a dramatically decreased rate of deactivation.

It is the object of this invention to provide a new catalyst for the catalytic hydrolysis of nitriles to amides with high conversions and selectivities for extended periods of time. This and other objects of the invention will become apparent to those skilled in the art from the following detailed description.

SUMMARY OF THE INVENTION

This invention relates to an improved process for the conversion of organic nitriles to amides, and more particularly to a catalytic hydrolysis of organic nitriles to the corresponding amides utilizing a supported complex of a rhodium compound and a thiophosphite as the heterogeneous catalyst. The preferred complexes are the complexes of rhodium trichloride and triethyltrithiophosphite or trilauryltrithiophosphite. The reaction is preferably carried out in the presence of an organic medium such as pyridine, a tertiary alcohol, tetramethylurea, hexamethylphosphoramide, cyclohexanone, aromatic hydrocarbons and mixtures thereof.

DESCRIPTION OF THE PREFERRED EMBODIMENTS

The nitriles which can be hydrolyzed by the process of this invention include any organic nitriles of the general formula RCN, where R can be alkyl, alkenyl, cycloalkyl, aryl or alkaryl and generally contains 1 to 20 carbon atoms. The R group can also be substituted by halogen, nitro, hydroxy, ester, carbonyl or cyano radicals. When two or more nitrile groups are present in the molecule, one or both may be converted to amide groups. Specific examples of such nitriles include acetonitrile, propionitrile, isobutyronitrile, stearonitrile, benzonitrile, p-chlorobenzonitrile, toluonitrile, benzoylacetonitrile, cyclohexylcyanide, p-cyanoacetophenone, acrylonitrile, 2-methyleneglutaronitrile, adiponitrile, 1,3-dicyanobutane and phthalonitrile.

The hydrolyzing agent or agents which can be employed include water and oxygenated substances such as alcohols of 1 to 5 carbon atoms such as methanol, ethanol, isopropanol, t-butanol and t-amyl alcohol, glycols of 1 to 6 carbon atoms such as ethylene glycol, propylene glycol and hexalene glycol, glycol monoethers such as the monoethers of ethylene glycol and diethylene glycol, and glycol monoesters such as the monoacetates. Water is the preferred hydrolytic agent. The molar ratio of the hydrolytic agent to nitrile can range from about 0.1:1 to 100:1, and is preferably about 1:1 to 10:1. Since the hydrolysis reaction is stoichiometric, whichever reactant is present in excess will act as a solvent for the reaction system.

The reaction can be conducted at a temperature of from about 25°-250° C., with a range of about 70°-160° C. being preferred, and a temperature of about 100°-130° C. being most preferred. The reaction can be conducted at any pressure from atmospheric to 5000 psi, with or without an inert gas, such as nitrogen, CO$_2$ or methane. The reaction is preferably conducted in the liquid phase although it can be performed in the vapor phase or in the "trickle" (mixed liquid-vapor) phase if desired.

The catalyst employed in the instant process is the reaction product of a rhodium compound and a thiophosphite. The rhodium compound can be any Rh$^{+3}$ salt such as the chloride, bromide, nitrate or acetylacetonate, any complex of a Rh$^{+3}$ salt such as the triacrylonitrile or tripyridine complexes of RhCl$_3$, any complex of a Rh$^{+1}$ salt such as the 1,5-cyclooctadiene complex of RhCl, and any complex of Rh° such as the cyclooctadiene complex of Rh. The preferred rhodium compound is a rhodium chloride, and mostly preferably RhCl$_3$.

The ligands of the present catalyst are of the formulas

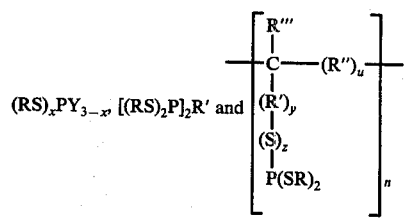

where R is alkyl of 1-20 carbon atoms or aryl of 6 to 12 carbon atoms or aralkyl of 7-13 carbon atoms; $x$ is 2 or 3; Y is OH or SH or halogen; R' is alkylene of 1-20 carbon atoms, arylene of 6–12 carbon atoms or a divalent aralkyl radical of 7–13 carbon atoms; R" is alkylene of 1–20 carbon atoms or arylene of 6–12 carbon atoms or a divalent aralkyl radical of 7–13 carbon atoms; R'" is H, alkyl of 1–20 carbon atoms, aryl of 6–12 carbon atoms or aralkyl of 7–13 carbon atoms; $y$ is 0 or 1; $z$ is 0 or 1; $u$ is 0 or 1; and $n$ is 3 to 100. Typical ligands include diethyldithiohypophosphorous acid, dilauryldithiohypophosphorous acid, dipropyldithiophosphinite, diphenyldithiophosphinite, ethylene bis(diethyldithiophosphite), phenylene bis(dilauryldithiophosphite), benzylene bis(dioctyldithiophosphite), Polythiophosphite (a polymeric thiophosphite of about 1000 molecular weight manufactured by Weston), triphenyltrithiophosphite, trinaphthyltrithiophosphite, and the like.

The preferred ligands are the trialkyltrithiophosphites in which the alkyl moieties contain 1 to about 20 carbon atoms. Typical compounds include trimethyltrithiophosphite, triethyltrithiophosphite, tripropyltrithiophosphite, tridecyltrithiophosphite, trilauryltrithiophosphite, and the like. The preferred trialkyltrithiophosphites are triethyltrithiophosphite (hereinafter TETTP) and trilauryltrithiophosphite (hereinafter TLTTP).

The ligands can be prepared by any of the processes known heretofore. The amount of such ligand used to prepare the catalyst can range from 0.5–10 mole equivalents based on the amount of rhodium compound. It is preferred to employ at least three, and more preferably at least four molar excess of the ligand over the rhodium compound. It is most preferred to use a 4:1 molar ratio of ligand to rhodium compound.

The complex catalyst of this invention can be impregnated on any of the known solid supports to form a heterogeneous catalyst system. Suitable supports include carbon, alumina, diatomaceous earth, silica, silica-magnesia, silica-alumina, zirconia, molecular sieves, organic cation exchange resins, chelating resins, ligand functionalized organic polymers, and the like. The concentration of the catalyst, in terms of the rhodium metal concentration on the support, can vary from about 0.01 to 20% and is preferably about 0.5 to 10%.

The catalyst complex of the instant invention can be prepared merely be bringing the rhodium compound and the ligand into contact in a suitable solvent, such as one or more of the cosolvents described below, preferably at elevated temperature. The heterogeneous catalyst can be prepared by contacting a preformed complex in a suitable solvent, such as one or more of the cosolvents described below, with the support, preferably at elevated temperature. For example, carbon, 5A and 13X molecular sieves have been utilized in this manner. Alternatively, a heterogeneous system can be prepared using insoluble polymeric ligands. For example, a chloromethylated polystyrene-divinylbenzene copolymer can be sequentially thiolated with thiourea, converted to thiophosphite by reaction with PCl$_3$, and coordinated with rhodium trichloride.

An alternate method of preparing a heterogeneous catalyst is by ion exchange of the rhodium into the support before addition of ligands. In this method, the first step is to incorporate the metal ion into the solid, for example, by heating the solids with a solution of rhodium compound. Once the metal ion is incorporated, it cannot be removed by refluxing solvents or water. The second step in this preparation is to react the bound rhodium with the desired ligand, either in one of the co-solvents described below before introduction of the catalyst into the reaction medium, or in the reaction mixture itself which will result in the in situ formation of the catalyst. There is a significant difference between trimethylphosphite and trialkyltrithiophosphites as coordinating ligands for the rhodium on 5A molecular sieves; in pyridine, trimethylphosphite leaches the metal ions from the sieves, resulting in a non-catalytic solid and a liquid syrup which is catalytic, whereas the trialkyltrithiophosphites exhibit the opposite behavior.

The catalysts of this invention are employed in a catalytic amount. For example, the liquid hourly space velocity can vary over a large range of about 0.01–50 ml nitrile/ml catalyst/hour, preferably about 0.05–5 ml nitrile/ml catalyst/hour. The hydrolysis can be effected under either acid or basic conditions although it is preferred to employ mildly basic media. Phosphites are hydrolyzed in stepwise fashion in acidic media to form phosphoric acid and alcohol which contributes to the deterioration of the catalyst. An analogous hydrolysis occurs with thiophosphites but at a much slower rate. the use of mildly basic media acts to retard the slow hydrolysis of the thiophosphites.

It was pointed out above that whichever of the hydrolyzing agent or nitrile is present in stoichiometric excess will act as a solvent for the reaction. It has also been found advantageous to employ certain co-solvents, namely pyridine, tertiary alcohols of 4–10 carbon atoms such as tert-butanol, tetramethylurea, hexamethylphosphoramide, cyclohexanone, aromatic hydrocarbons such as toluene, benzene, xylene, ethylbenzene, cumene, cymene, mesitylene, and mixtures thereof. Pyridine is a preferred co-solvent since it has been found that the presence of pyridine, even in minor concentrations, produces a profound effect on the hydrolysis rate using various coordinated rhodium catalysts. Certain mixtures of solvents afford special features which can be used advantageously and among these, the acrylonitrile-pyridine, pyridine-toluene, and pyridine-toluene-acrylonitrile systems deserve mention. The amount of the co-solvent which can be used varies over a large range and generally can be about 3–98 weight percent based on the liquid phase and preferably about 15–85 weight percent.

In some preferred embodiments of the invention, it has been found advantageous to employ a small amount of a catalyst promoter. Suitable promoters include phenol, lauryl mercaptan, and (C$_6$H$_5$)$_3$PO. These promoters can be utilized in amounts which can range from a very small molar fraction (e.g., 0.1 mole) up to about 1 mole per mole of catalyst.

In order to further illustrate the invention, various Examples are given hereinafter. Throughout this specification and claims, all parts and percentages are by weight and all temperatures are in degrees centigrade unless otherwise specified. In these Examples, relative yields are given in relation to the identical procedure performed without the rhodium catalyst but with the ligand.

EXAMPLE 1

Into 10 ml stainless steel tubes were charged 0.1 mmole RhCl$_3$.3H$_2$O, 0.4 mmole TLTTP, 4 ml pyridine, 1–2 g of nitrile and a stoichiometric equivalent amount of water. The tubes were pressurized to 150 psig with nitrogen and heated at 120° C. for 17 hours and then the products were determined. In this manner, benzonitrile was converted to benzamide and nicotinonitrile was converted to nicotinamide. These reactions were repeated on a scale up of about 10-times using methyleneglutaronitrile as the nitrile, 115° C. for 27 hours and a nitrogen pressure of 210 psig to produce 2-methyleneglutaramide.

EXAMPLE 2

In order to compare the effect of various ligands, acrylonitrile was hydrolyzed to acrylamide in agitated reactors containing excess acrylonitrile as solvent at 120° C. with a catalyst of 0.23 mmole rhodium trichloride trihydrate and 0.8 mmole of ligand. One set of reactions were carried out in unpressurized reactors using an initial charge of 10 ml acrylonitrile and 1 ml water followed by the addition of 5 ml acrylonitrile and 1 ml water at the 30 hours mark. A second set of reactions were carried out in pressurized reactors using an initial charge of 15 ml acrylonitrile and 2 ml water and a nitrogen pressure of 50 psig. The time in hours, ligand used, acrylamide produced in grams, and catalyst efficiency in grams amide/grams rhodium/hour are reported in Table I.

TABLE I

| | | LIGAND | | | |
|---|---|---|---|---|---|
| | Time | $(CH_3O)_3P$ | $(Decyl-O)_3P$ | TETTP | TLTTP |
| Unpressurized Reactors | | | | | |
| Acrylamide produced, grams | 5 | 0.4 | 1.2 | 0.4 | 0.2 |
| | 10 | 0.5 | 1.5 | 0.9 | 0.4 |
| | 20 | 0.6 | 1.6 | 1.5 | 0.8 |
| | 30 | 0.9 | 1.7 | 2.0 | 1.7 |
| | 50 | 1.0 | 1.7 | 3.2 | 3.7 |
| Catalyst efficiency | 0–5 | 3.2 | 9.4 | 3.0 | 1.7 |
| | 5–10 | 1.0 | 2.3 | 4.0 | 1.7 |
| | 10–20 | 0.3 | 0.4 | 2.6 | 1.4 |
| | 20–30 | 1.1 | 0.7 | 1.8 | 3.8 |
| | 30–50 | 0.2 | 0.0 | 2.5 | 4.0 |
| | 0–50 | 0.8 | 1.4 | 2.6 | 3.0 |
| Pressurized Reactors | | | | | |
| Acrylamide produced, grams | 10 | 3.05 | 2.01 | 3.40 | 2.12 |
| | 20 | 3.10 | 2.49 | 6.80 | 5.05 |
| Catalyst efficiency | 0—10 | 12.2 | 8.0 | 13.6 | 8.5 |
| | 10–20 | 0.2 | 1.9 | 13.6 | 11.7 |
| | 0–20 | 6.2 | 5.0 | 13.6 | 10.1 |

EXAMPLE 3

Acrylonitrile was hydrolyzed to acrylamide by charging 2 ml acrylonitrile, 0.55 ml water and 4 ml t-butanol into 10 ml stainless steel tubes which were then pressurized to 225 psig with nitrogen and heated to 120° C. The catalyst employed was 0.2 mmole $RhCl_3.3H_2O$ complex with 0.8 mmole of ligand. When the ligand employed was TLTTP, the relative acrylamide yield was 59 at the end of 18 hours. When $(CH_3O)_3P$ was used as the ligand, the relative acrylamide yield was 3.6 at the end of 66 hours.

EXAMPLE 4

Example 3 was repeated except that the nitrogen pressure was 100–250 psi. The relative acrylamide yields at the end of 18 hours for the following ligands were found:

| Ligand | Relative Yield |
|---|---|
| $(C_6H_5O)_3P$ | 5.7 |
| $(Allyl-O)_3P$ | 20 |
| $(Decyl-O)_3P$ | 8.1 |
| TLTTP | 59 |

EXAMPLE 5

Example 4 was repeated except that pyridine was used as a co-solvent. The relative acrylamide yields found using three ligands were:

| Ligand | Relative Yield |
|---|---|
| $(CH_3O)_3P$ | 17 |
| $(Allyl-O)_3P$ | 13 |
| TLTTP | 47 |

EXAMPLE 6

A catalyst containing 0.1 mmole $RhCl_3.3H_2O$, 0.4 mmole ligand, 0.34 ml water, 5 ml acrylonitrile and 1 ml pyridine were reacted in stainless steel reactors at 120° C. under 100 psig of nitrogen. The results are shown in Table II.

TABLE II

| | | LIGAND | |
|---|---|---|---|
| | Time, Hours | $(CH_3O)_3P$ | TETTP | TLTTP |
| Acrylamide yield, % | 3 | 35 | 50 | 32 |
| | 6 | 48 | 81 | 52 |
| | 21 | 46 | 83 | 92 |
| Selectivity, % | 3 | 81 | 77 | 87 |
| | 6 | 83 | — | 93 |
| | 21 | 35 | 69 | 84 |

EXAMPLE 7

Linde 5A molecular sieves were impregnated with rhodium by heating in an aqueous solution of (color removed) rhodium trichloride hydrate. The isolated dry solid, containing 0.031 gram rhodium trichloride hydrate/gram was divided in half and no further treatment was performed on the first portion of the catalyst (A). The second portion (B) of the material was heated at reflux with an excess of TETTP in pyridine, filtered, washed with pyridine and dried.

0.2 Gram each of A and B and 10 ml of acrylonitrile, 2 ml $H_2O$, 2 ml pyridine, and 0.6 gram of durene (internal standard for GLC analysis) were charged into 2 stainless steel reactors under a nitrogen atmosphere. The sealed reactors were heated under autogeneous pressure at 120° C. for 15 hours with vigorous agitation. GLC analysis showed 0.2 gram of acrylamide formed with catalyst B and no acrylamide formed with catalyst A.

EXAMPLE 8

1.6 Gram of catalyst B of Example 7, 20 ml acrylonitrile, 2 ml water, 2 ml pyridine and 1.12 grams of durene were charged into a stainless steel reactor which was then pressurized to 50 psig with nitrogen and heated at 120° C. for 10 hours with vigorous agitation. GLC analysis showed 0.97 grams of acrylamide was formed.

EXAMPLE 9

1 Gram of rhodium trichloride hydrate was dissolved in 10 ml of refluxing pyridine under nitrogen, 10 ml of TLTTP were added and the mixture was refluxed for 5.5 hours. The resulting red solution was poured into a 25 ml volumetric flask and diluted to volume with pyridine. 1 ml of this solution was mixed with 2 grams of Linde 4A molecular sieves under nitrogen at room temperature. The filtered and washed solid was charged under nitrogen into a stainless steel reactor together with 10 ml acrylonitrile, 1 ml water, 1 ml pyridine and 0.6 gram of durene. The reactor was heated under autogeneous pressure at 120° C. with vigorous shaking for 15 hours at which time GLC analysis showed 1.22 grams of acrylamide had been formed.

The catalyst was filtered, washed with acetone, dried and reused as above. 0.98 gram of acrylamide was formed.

EXAMPLE 10

5 Grams of Amberlite 200 cation exchange resin (Na+ form) beads were heated to reflux in a solution of 0.1 gram rhodium trichloride hydrate in water. After about 0.5 hour, the solution had become colorless. The resin was filtered, washed and dried. 2 Grams of the beads were then charged into each of 2 stainless steel reactors under nitrogen together with 15 ml acrylonitrile, 2 ml water and 0.84 gram durene. Into one reactor (A) was added 0.4 ml of TLTTP and into the second reactor (B) was added 0.16 ml of TETTP. Both reactors were heated to 120° C. under 50 psig of nitrogen for 10 hours with constant agitation. Small samples were discharged for GLC analysis. Reaction mixture A was found to contain 0.86 gram of acrylamide (11% yield) and B contained 1.52 grams of acrylamide (19.5% yield). The reaction was continued for another 10 hours, 1.03 grams of additional acrylamide being formed in mixture A (24% total yield) and 1.43 grams of acrylamide being formed in mixture B (38% total yield).

The solid catalyst was then filtered from each reaction mixture, rinsed with acrylonitrile, dried and reacted as previously for 16.5 hours. 0.83 And 0.93 grams of acrylamide were formed using the solids from A and B respectively.

EXAMPLE 11

1 gram of rhodium trichloride hydrate was dissolved in 25 ml of n-propanol and 1 ml of pyridine was added, resulting in a pink precipitate. The mixture was heated to reflux and then 9 ml of TLTTP were added and the mixture refluxed for 3 hours. The precipitate dissolved and a deep red solution resulted. The red solution was poured into a 100 ml volumetric flask and diluted to 100 ml with toluene.

2.5 Grams of Nuchar C-145-N activated carbon was mixed with 10 ml of catalyst solution and the mixture dried. 0.4 Gram of the resulting catalyst was mixed with 10 ml acrylonitrile, 1 ml water, 2 ml pyridine and 0.6 gram durene under nitrogen in a stainless steel reactor. The reactor was heated to 120° C. for 19.5 hours under autogeneous pressure with constant agitation at which time GLC analysis showed an 11.7% yield of acrylamide.

EXAMPLE 12

A mercaptan functionalized resin was prepared by refluxing 5 grams of chloromethylated polystyrene with 1% divinylbenzene cross-linked beads in 35 ml of 95% ethanol with 0.5 gram of thiourea for 28 hours. 0.4 Gram of NaOH in 6 ml water was added and the mixture refluxed for 2.5 hours. The polymer was then filtered, washed and dried and dispersed in 50 ml of di-n-butylether and 2.4 ml of N,N-dimethylaniline in a 3-necked nitrogen swept flask. A solution of 0.86 gram of $PCl_3$ in 10 ml di-n-butylether was added dropwise to the flask, chilled to 5° C., then a solution of 2.6 grams of laurylmercaptan in 10 ml of di-n-butylether was added. The resulting thiophosphite functionalized resin was then filtered, washed with successive portions of toluene, hexane, methanol, water and methanol and finally dried.

0.1 Gram of rhodium trichloride hydrate was dissolved in 24 ml n-propanol and 0.15 ml of N,N-dimethylaniline. The thiophosphite functionalized resin was added to the solution and the mixture heated to reflux under nitrogen for about 2 hours. The solid was filtered, washed with propanol and methanol and then dried.

2 Grams of the resulting solid catalyst, 20 ml of acrylonitrile, 2 ml of water, 2 ml of pyridine, and 0.5 gram of durene were charged into a stainless steel vessel under nitrogen. The mixture was heated at 150° C. for 18 hours under 50 psig of nitrogen with constant agitation. GLC analysis showed 1.01 grams of acrylamide had been formed.

EXAMPLE 13

10 ml of silica-magnesia extrusions were heated in a boiling solution of 0.3 gram of rhodium trichloride hydrate in water until the solution was colorless. The extrusions were then water-washed and oven dried. 5 ml of the impregnated extrusions, 1.4 ml of TLTTP, 20 ml of acrylonitrile and 4 ml of water were charged into a stainless steel vessel which was then pressurized to 100 psig with nitrogen. The reactor was heated at 120° C. with constant shaking for 17 hours and then the contents were discharged and volatiles evaporated. The solid residue was washed with toluene, hexane and dried to yield 1.6 grams of acrylamide.

EXAMPLE 14

4.85 Grams of Linde 5A molecular sieves in 25 ml of $H_2O$ were heated and mixed with 2 ml of a water solution (A) containing 0.0305 gram $RhCl_3.3H_2O$/ml. As the solution color disappeared, successive 2 ml and 3 ml additions of A were made over a 2 hour period. The now powdered brown solid (B) was filtered, washed with acetone and dried in an oven at 130° C. for 1 hour.

2.50 grams of B, 5 ml of pyridine, and 5 ml of TETTP were heated at reflux under $N_2$ for 63 hours. The mixture was cooled and filtered. The solid was washed with pyridine, methanol and air dried. The weight of greenish-yellow solid, C, was 2.85 grams.

1.0 Gram each of solids B and C were heated at reflux with 5 ml of acrylonitrile, 1 ml of pyridine, and 0.5 ml of $H_2O$. With solid B, no acrylamide was formed. With solid C, acrylamide was formed at a rate of 5.5 g/g Rh/hr.

EXAMPLE 15

Following the procedure of Example 14, trimethylphosphite was used in place of TETTP. However, after a short period at reflux, the supernatant liquid had turned deep red. The mixture was filtered and the solid washed and dried. When reacted as in Example 14 with acrylonitrile and water, no acrylamide was formed in the presence of the solid, but acrylamide was formed with the red filtrate.

EXAMPLE 16

4.42 Grams of Linde 5A molecular sieves were impregnated with 0.50 gram of $RhCl_3.3H_2O$ by the method of Example 7. In a stainless steel reactor (A) were charged 1.5 grams of the dry powder, 0.4 ml of TETTP, 20 ml of acrylonitrile, 2 ml of $H_2O$, and 1.12 grams of durene. The same charge plus 2 ml of pyridine was loaded into reactor B. The reactors were heated at 120° C. with agitation for 10 hours under 50 psig of $N_2$. GLC analysis showed 1.97 grams of acrylamide had been formed in reactor A while B had produced 2.85 grams of acrylamide.

EXAMPLE 17

10.0 Grams of Harshaw zirconia tablets were heated sequentially in separate boiling water solutions of 0.10 gram of $RhCl_3.3H_2O$ with a water wash between the ion exchange impregnations. The dried solid was then heated for 3 hours under nitrogen in a refluxing solution of 3 ml of TETTP in 20 ml of pyridine. The supernatant liquid was poured into stainless steel reactor A under nitrogen together with 5 ml of acrylonitrile and 2 ml of $H_2O$. The solid catalyst was washed with pyridine and the solvent evaporated under nitrogen and then charged into reactor B together with 15 ml of acrylonitrile and 5 ml of $H_2O$. The reactors were heated (with agitation) at 120° C. under 100 psig of nitrogen for 15 hours. GLC analysis showed 2.70 grams of acrylamide in B, but none in A.

EXAMPLE 18

21.7 Grams of Davison Grade 542 10 A pore size molecular sieve beads were heated in a boiling water solution containing 0.50 gram of $RhCl_3.3H_2O$. The solid was filtered, washed, then impregnated with a fresh solution as above. The solid was thoroughly re-washed and dried. The impregnated sieves were heated at reflux under nitrogen in a solution of 10 ml of TLTTP in 25 ml of pyridine for 7 hours. Supernatant liquid was removed by decantation and then the solid washed repeatedly with pyridine and dried under nitrogen. 25 ml of this catalyst were charged into a continuous tubular reactor. With the catalyst bed at 130° C. and a reactor pressure of 140 psig, a feed of 72.5% acrylonitrile, 9.1% $H_2O$, and 18.4% pyridine was fed at a liquid hourly space velocity of 1.48. A space time yield of 20 mg acrylamide/ml catalyst/hour was obtained.

EXAMPLE 19

25 ml of Linde 5A molecular sieves were impregnated with rhodium by two successive treatments with boiling water solutions containing 1.00 gram of $RhCl_3.3H_2O$. After washing with water, acetone, and methanol, the solid was dried and charged into a continuous reactor. 22 ml of a solution of 50 ml acrylonitrile, 10 ml pyridine, and 8 ml TETTP were fed into the reactor which was then heated to 120° C. under 105 psig of $N_2$. The remainder of the solution was fed through the reactor over a period of 3 hours. Then a reaction solution of 73% acrylonitrile, 9% $H_2O$, and 18% pyridine was fed into the reactor at total liquid hourly space velocities ranging from 1.2–2.5 with catalyst bed temperatures of 135°–163° C. and reactor pressure of 105 psig. Space time yields of 84–230 mg/ml catalyst/hour were obtained.

EXAMPLE 20

36.2 grams of Linde 5A molecular sieve extrusions were treated with successive boiling water solutions containing 1.00 gram of $RhCl_3.3H_2O$. The yellow extrusions were washed with water and acetone, then dried. One-half of the catalyst was then reacted with 2.5 ml of TETTP in 30 ml of refluxing pyridine for 1.5 hours. Supernatant liquid was removed by filtration under nitrogen. The dark green solid was rinsed with pyridine, dried under nitrogen and charged into the reactor. With a solution of 70% acrylonitrile, 9% $H_2O$ and 21% pyridine being fed at a liquid hourly space velocity of 1.5, and bed temperature of 130° C., and reactor pressure of 143 psig, a space time yield of 50 mg acrylamide/ml catalyst/hour was obtained.

EXAMPLE 21

By the method of Example 5, acrylonitrile was hydrolyzed using 0.1 mmole of $RhCl_3.3H_2O$ and 0.3 mmole of Weston 93-P, a low melting polythiophosphite of about 1000 molecular weight, as catalyst. An 18% yield of acrylamide was obtained after 16 hours.

Various changes and modifications can be made in the present invention without departing from the spirit and the scope thereof. The various embodiments set forth herein were for the purpose of further illustrating the invention but were not intended to limit it.

We claim:
1. In a method for the catalytic hydrolysis of nicotinonitrile or a nitrile of the formula RCN wherein R is an alkyl, alkenyl, cycloalkyl, aryl or alkaryl radical of 1–20 carbon atoms or said radical substituted by halogen, nitro, hydroxy, benzoyl, acetyl or cyano groups to the corresponding amide, the improvement which comprises employing as the catalyst, an effective catalytic amount of the reaction product of rhodium trichloride and a trialkyltrithiophosphite supported on a solid support selected from the group consisting of carbon, alumina, diatomaceous earth, silica, silica-magnesia, silica-alumina, zirconia, molecular sieves, organic cation exchange resins, chelating resins and ligand functionalized polymers.

2. The method of claim 1 wherein said hydrolysis is conducted in the presence of an organic medium selected from the group consisting of pyridine, tertiary alcohols, tetramethylurea, hexamethylphosphoramide, cyclohexanone, aromatic hydrocarbons and mixtures thereof.

3. The method of claim 1 wherein said hydrolysis is conducted in the presence of a catalyst promoter selected from the group consisting of phenol, laurylmercaptan and $(C_6H_5)_3PO$.

4. The method of claim 1 wherein said trialkyltrithiophosphite is triethyltrithiophosphite.

5. The method of claim 1 wherein said trialkyltrithiophosphite is trilauryltrithiophosphite.

6. The method of claim 1 wherein the concentration of catalyst, in terms of the rhodium concentration on the support, is about 0.01 to 20 weight percent.

7. The method of claim 6 wherein the concentration is about 0.5–10 weight percent.

8. The method of claim 1 wherein the liquid hourly space velocity is about 0.01–50 volumes nitrile/volume catalyst/hour.

9. The method of claim 8 wherein the liquid hourly space velocity is about 0.05 to 5 volumes nitrile/volume catalyst/hour.

10. The method of claim 1 wherein said catalyst is the reaction product of rhodium trichloride and a trialkyltrithiophosphite selected from the group consisting of triethyltrithiophosphite and trilauryltrithiophosphite.

11. The method of claim 10 wherein the liquid hourly space velocity is about 0.01–50 volumes nitrile/volume catalyst/hour.

12. The method of claim 11 wherein the liquid hourly space velocity is about 0.05 to 5 volumes nitrile/volume catalyst/hour.

13. The method of claim 10 wherein said hydrolysis is conducted in the presence of an organic medium selected from the group consisting of pyridine, tertiary alcohol, tetramethylurea, hexamethylphosphoramide, cyclohexanone, toluene, benzene, xylene, ethylbenzene, cumene, cymene, mesitylene, and mixtures thereof.

* * * * *